United States Patent [19]

Renken et al.

[11] Patent Number: 4,532,324

[45] Date of Patent: Jul. 30, 1985

[54] CATALYTIC PROCESS FOR THE COPRODUCTION OF MORPHOLINE AND 2-(2-HYDROXYETHOXY)ETHYLAMINE FROM DIETHYLENE GLYCOL

[75] Inventors: Terry L. Renken; John R. Sanderson, both of Austin, Tex.

[73] Assignee: Texaco, Inc., White Plains, N.Y.

[21] Appl. No.: 573,772

[22] Filed: Jan. 25, 1984

[51] Int. Cl.³ .......................................... C07D 295/02
[52] U.S. Cl. ..................................... 544/106; 564/480
[58] Field of Search ......................................... 544/106

[56] References Cited

U.S. PATENT DOCUMENTS

| | | | |
|---|---|---|---|
| 3,151,112 | 9/1964 | Moss | 544/106 |
| 3,152,998 | 10/1964 | Moss | 252/470 |
| 3,155,657 | 11/1964 | Bedoit | 544/106 |
| 4,153,581 | 5/1979 | Habermann | 252/472 |

FOREIGN PATENT DOCUMENTS 1361363  7/1974  United Kingdom .

Primary Examiner—Robert W. Ramsuer
Attorney, Agent, or Firm—Jack Park; Kenneth R. Priem

[57] ABSTRACT

An enhanced yield of 2-(2-hydroxyethoxy)ethylamine is obtainable when diethylene glycol is reductively aminated over a catalyst consisting of cobalt, copper and ceria or thoria or a mixture thereof.

5 Claims, No Drawings

CATALYTIC PROCESS FOR THE COPRODUCTION OF MORPHOLINE AND 2-(2-HYDROXYETHOXY)ETHYLAMINE FROM DIETHYLENE GLYCOL

BACKGROUND OF THE INVENTION

1. Field of the Invention

This invention relates to an improved process for the coproduction of morpholine and 2-(2-hydroxyethoxy)ethyl amine from diethylene glycol. More particularly, this invention relates to a process for the catalytic reductive amination of diethylene glycol for the coproduction of morpholine and 2-(2-hydroxyethoxy)ethyl amine wherein the catalyst that is used consists of cobalt, copper and ceria and/or thoria whereby an enhanced yield of 2-(2-hydroxyethoxy)ethyl amine is obtained.

2. Prior Art

It has heretofore been proposed to prepare morpholine from diethylene glycol by reductive aminolysis as shown, for example by Moss U.S. Pat. No. 3,151,112 which is specifically directed to such a process and Moss U.S. Pat. No. 3,152,998, Habermann U.S. Pat. No. 4,153,581 and British Pat. No. 1,361,363 which disclose reductive amination processes wherein diethylene glycol is mentioned as a feed component.

Another relevant patent is Bedoit U.S. Pat. No. 3,155,657 which is also directed to the coproduction of morpholine and 2-(2-hydroxyethoxy)ethyl amine.

As exemplified by these patents, a wide variety of metals and metal oxides have been proposed for use as catalysts in the reductive amination of feedstocks containing one or more hydroxy groups.

Also, as exemplified by the prior art mentioned above, each particular catalyst system can be characterized as having a unique product distribution for the feedstock with which it is employed. Changes in product distribution, and hence, product selectivity, can normally be accomplished only within comparitively narrow limits.

Morpholine is an article of commerce which is widely used in the preparation of accelerators for curing rubber, optical brighteners for fabrics, etc.

2-(2-Hydroxyethoxy)ethyl amine, which is sold commercially, for example by Texaco Inc., under the trademark DIGLYCOLAMINE ®, is also an article of commerce useful for a variety of purposes such as the sweetening of sour natural gas, the treatment of transformer paper, etc.

When morpholine is manufactured as taught by Moss U.S. Pat. No. 3,151,112, one of the coproducts that is formed is 2-(2-hydroxyethoxy)ethyl amine. However, for any specific conversion of diethylene glycol, there is only a comparitively narrow limit within which the ratio of morpholine to 2-(2-hydroxyethoxy)ethyl amine can be varied.

Accordingly, there is a need for a process wherein relatively greater amounts of 2-(2-hydroxyethoxy)ethyl amine can be prepared from a given quantity of feedstock when market conditions so demand.

SUMMARY OF THE INVENTION

It has been surprisingly discovered, in accordance with the present invention, that when diethylene glycol is reductively aminated in the presence of a catalyst consisting cobalt, copper and ceria and/or toria, the resultant product contains, for a given set of reaction conditions, an enhanced amount of 2-(2-hydroxyethoxy)ethyl amine, as compared with the amounts heretofore obtainable.

The feedstock for the present invention is diethylene glycol.

The catalyst to be used in accordance with the present invention consists of a mixture of cobalt and copper containing from about 25 to about 94 wt.% of cobalt from about 5 to about 74 wt.% of copper and correspondingly, from about 1 to about 40 wt.% of ceria or thoria or a mixture thereof.

The catalyst of the present invention may be prepared by conventional techniques such as one wherein salts of the metals to be employed in the final catalyst are first coprecipitated from an aqueous solution. This precipitated material is then dried and calcined to form the corresponding oxides. Thereafter, the catalyst is prepared for use by reducing the cobalt and copper oxides to metallic cobalt and copper (e.g., with hydrogen). The cerium oxide (ceria) and/or thorium oxide (thoria) will remain present in the final composition in the oxide form.

The cobalt-copper catalyst of the present invention is preferably used as such, but may be supported on any of the commonly used inert supports that are used for this purpose such as alumina, silica, keiselguhr, titania, etc.

The process of the present invention is suitably conducted at a temperature within the range of about 150° to about 260° C. and at a pressure within the range of about 500 to about 3500 psig.

The reductive amination of the diethylene glycol is conducted in the presence of ammonia. From about 1 to about 50 moles of ammonia per mole of diethylene glycol are employed and more preferably, from about 4 to about 8 moles.

The reaction is generally conducted in the presence of added hydrogen. The amount of hydrogen used may be about 0.01 to about 1.0 mole per mole of diethylene glycol. Preferably, about 0.05 to about 0.3 mole of hydrogen per mole of diethylene glycol is employed.

The process of the present invention may be conducted batchwise using an autoclave containing powdered catalyst, or may be conducted continuously by passing the feed materials over a bed of pelleted catalyst. When the process of the present invention is conducted continuously, the desired molar ratios of ammonia and hydrogen to diethylene glycol can be established and maintained by regulation of the rates at which the feed components are fed to the reactor.

The reaction mixture formed as a result of the reductive amination of the diethylene glycol may be recovered and fractionated in any suitable manner, such as by fractional distillation, to obtain unreacted diethylene glycol which may be recycled, morpholine, 2-(2-hydroxyethoxy)ethyl amine and other by-products.

DETAILED DESCRIPTION OF THE PREFERRED EMBODIMENT OF THE PRESENT INVENTION

The present invention is further illustrated by the following specific examples which are given by way of illustration and which are not intended as limitations on the scope of this invention.

EXAMPLE 1

Co-Cu-Ce Catalyst Preparation

A solution composed of cobalt (II) nitrate hexahydrate (709 g), copper (II) nitrate hydrate (122 g) and ceric ammonium nitrate (82 g) in 1500 ml of deionized (DI) water and a solution of sodium carbonate (425 g) in 2000 ml of deionized water were added simultaneously over 1.5 hours to 1000 ml of rapidly stirred deionized water at 70°–80° C. The rates of addition were adjusted so the pH of the solution remained at ca. 7.0. After 1 hour of stirring at 80° C. the precipitated carbonates were removed by filtration. The filter cake was washed by adding it to 2000 ml of fresh DI water and heating the resultant slurry to 80° C. with rapid stirring, followed by filtration. The washing and filtration steps were repeated six additional times. The filter cake was dried in air at 110° C. and then calcined at 400° C. to decompose the carbonates. The resultant metal oxide mixture (270 g) was reduced in a hydrogen/nitrogen stream at 300° C., followed by partial oxidation at 25°–65° C. with a stream of air/nitrogen to stabilize the catalyst to atmospheric conditions. The resultant powder contained 70.0 wt.% Co, 14.0 wt.% Cu and 9.7 wt.% Ce. Graphite (1%) was added to a portion of the catalyst and this material was formed into 5/32 inch pellets.

Amination of Diethylene Glycol

Pelleted catalyst (86 cc) was charged to an upward flow 0.516 inch ID tubular reactor. A premixed feed composed of 6/1 (mol/mol) ammonia/diethylene glycol (DEG) was pumped through the catalyst bed at a rate of ca. 0.57 lb/hr. Hydrogen was also passed through the reactor at 2.1 l/hr (flow calibrated for 0° C. and 1 atmosphere pressure corresponding to a molar ratio of about 0.075 mole of hydrogen per mole of diethylene glycol). The reactor pressure was maintained at 2500 psig. Liquid samples corresponding to several reactor temperatures were analyzed by gas chromatography on an ammonia and water free basis. The results of these analyses along with the appropriate reactor conditions are given below in Table 1.

TABLE 1

| Temp. °C. | 215 | 225 | 235 | 245 |
|---|---|---|---|---|
| LHSV, g/hr/cc cat | 3.1 | 3.0 | 3.1 | 3.0 |
| % DEG conversion | 41.1 | 47.5 | 51.7 | 57.1 |
| Selectivities: | | | | |
| 2-(2-Hydroxyethoxy) Ethylamine | 69.3 | 62.7 | 64.6 | 54.0 |
| Morpholine | 21.7 | 31.0 | 28.0 | 32.5 |
| Ratio: 2-(2-Hydroxyethoxy)ethylamine/ Morpholine | 3.2 | 2.0 | 2.3 | 1.7 |

EXAMPLE 2

Co-Cu-Th Catalyst Preparation

A solution composed of cobalt (II) nitrate hexahydrate (709 g), copper (II) nitrate hydrate (122 g) and thorium (IV) nitrate tetrahydrate (83 g) in 1500 ml of deionized (DI) water and a solution of sodium carbonate (415 g) in DI water were added simultaneously over 1.5 hour to 1000 ml of rapidly stirred DI water at 70°–80° C. The rates of addition were adjusted so the solution pH remained at ca. 7.0. After 1 hour of stirring at 80° C. the precipitated carbonates were removed by filtration. The filter cake was washed by adding it to 2000 ml of fresh DI water and heating the resultant slurry to 80° C. with rapid stirring, followed by filtration. The washing and filtration steps were repeated six additional times. The filter cake was dried in air at 110° C. and then calcined at 400° C. to decompose the carbonates. The resultant metal oxide mixture (278 g) was reduced in a hydrogen/nitrogen stream at 300° C., followed by partial oxidation at 25°–65° C. with a stream of air/nitrogen to stabilize the catalyst to atmospheric conditions (241 g total). The resultant powder contained 60.0 wt.% Co, 13.0 wt.% Cu and 13.2 wt.% Th. Graphite (1%) was added to a portion of the catalyst and this material was formed into 5/32 inch pellets.

Amination of Diethylene Glycol

Pelleted catalyst (82 cc) was charged to the tubular reactor. A premixed feed composed of 6/1 (mol/mol) ammonia/diethylene glycol (DEG) was pumped through the catalyst bed at a rate of ca. 0.54 lb/hr. Hydrogen was also passed through the reactor at 2.0 l/hr (flow calibrated for 0° C. and 1 atmosphere pressure corresponding to a molar ratio of about 0.075 mole of hydrogen per mole of diethylene glycol). The reactor pressure was maintained at 2500 psig. Liquid samples corresponding to several reactor temperatures were analyzed by gas chromatography on an ammonia and water free basis. The results of these analyses along with the appropriate reactor conditions are given below in Table 2.

TABLE 2

| Temp. °C. | 200 | 210 | 220 | 230 | 240 |
|---|---|---|---|---|---|
| LHSV, g/hr/cc cat | 3.0 | 2.9 | 2.8 | 3.0 | 2.9 |
| % DEG conversion | 26.3 | 38.4 | 45.9 | 51.4 | 59.1 |
| Selectivities: | | | | | |
| 2-(2-Hydroxyethoxy) Ethylamine | 78.7 | 73.4 | 65.9 | 63.4 | 57.8 |
| Morpholine | 15.9 | 21.9 | 27.9 | 29.2 | 31.4 |
| Ratio: 2-(2-Hydroxyethoxy)ethylamine/ Morpholine | 5.0 | 3.4 | 2.4 | 2.2 | 1.8 |

EXAMPLE 3

Commercial Ni-Cu-Cr catalyst (Harshaw Chemical Co., Ni 2715, 89 cc of 3/16 inch pellets) was charged to the tubular reactor. A premixed feed composed of 6/1 (mol/mol) ammonia/diethylene glycol (DEG) was pumped through the catalyst bed at a rate of ca. 0.66 lb/hr. Hydrogen was also passed through the reactor at 2.4 l/hr (flow calibrated for 0° C. and 1 atmosphere pressure corresponding to a molar ratio of about 0.075 mole of hydrogen per mole of diethylene glycol). The reactor pressure was maintained at 2500 psig. Liquid samples corresponding to several reactor temperatures were analyzed by gas chromatography on an ammonia and water free basis. The results of these analyses along with the appropriate reactor conditions are given below in Table 3.

TABLE 3

| Temp. °C. | 200 | 210 | 220 | 230 | 240 | 250 |
|---|---|---|---|---|---|---|
| LHSV, g/hr/cc cat | 3.4 | 3.4 | 3.3 | 3.4 | 3.3 | 3.4 |
| % DEG conversion | 12.2 | 17.3 | 33.1 | 49.5 | 65.1 | 78.7 |
| Selectivities: | | | | | | |
| 2-(2-Hydroxyethoxy) Ethylamine | 69.0 | 67.0 | 57.8 | 49.9 | 39.7 | 28.1 |
| Morpholine | 23.4 | 29.2 | 38.7 | 46.4 | 56.0 | 64.8 |
| Ratio: 2-(2-Hydroxyethoxy)ethylamine/ | 3.0 | 2.3 | 1.5 | 1.1 | 0.71 | 0.43 |

TABLE 3-continued

Morpholine

As can be seen from the examples, when the results obtained with the catalyst of the present invention (Examples 1 and 2) are compared with those obtained with the catalyst indicated by Moss to be preferable for the reaction (Example 3), an enhanced yield of 2-(2-hydroxyethoxy)ethyl amine is obtained for the specific degree of conversion of diethylene glycol involved.

For example, at a conversion level of diethylene glycol of 49.5%, the Moss et al. yield of 2-(2-hydroxyethoxy)ethyl amine was about 50%. However, at about the same conversions, there was a significant improvement in the yield insofar as the use of the catalyst of the present invention is concerned. Thus, in Example 1, at a diethylene glycol conversion of 47.5%, the yield of 2-(2-hydroxyethoxy)ethyl amine (DGA) was 62.7%. In Example 2 at diethylene glycol conversions of 45.9% and 51.4%, the yields of DGA were about 66% and 63%, respectively.

Having thus described my invention, what is claimed is:

1. In the catalytic reductive amination of diethylene glycol for the coproduction of morpholine and 2-(2-hydroxyethoxy)ethyl amine, the improvement for obtaining an enhanced yield of 2-(2-hydroxyethoxy)ethyl amine which comprises the step of: conducting said reductive amination of diethylene glycol in the presence of a catalyst consisting of cobalt, copper and ceria and/or thoria.

2. In a method as in claim 1, the improvement which comprises using a catalyst consisting of from about 25 to about 94 wt.% cobalt, from about 5 to about 74 wt.% of copper and correspondingly, about 1 to about 40 wt.% of ceria or thoria or both.

3. In a method as in claim 1, the improvement which comprises using a catalyst consisting of from about 60 to about 85 wt.% of cobalt, from about 10 to about 30 wt.% of copper and correspondingly, about 5 to about 20 wt.% of ceria or thoria or both.

4. A method for the coproduction of morpholine and 2-(2-hydroxyethoxy)ethyl amine which comprises contacting diethylene glycol with a catalyst consisting of cobalt, copper and ceria and/or thoria in the presence of ammonia and hydrogen under reductive amination conditions including a temperature within the range of about 150° to about 260° C. and a pressure within the range of about 500 to about 3500 psig. whereby an enhanced yield of 2-(2-hydroxyethyoxy)ethyl amine is obtained.

5. A method as in claim 4 wherein the molar ratio of ammonia to diethylene glycol is within the range of about 1 to about 50, wherein the molar ratio of hydrogen to diethylene glycol is within the range of about 0.01 to about 1.0 percent and wherein the catalyst consists of about 25 to about 94 wt.% of cobalt, about 5 to about 74 wt.% of copper and correspondingly, about 1 to about 40 wt.% of ceria or thoria.

* * * * *